United States Patent
Rohrer et al.

(10) Patent No.: US 8,921,427 B2
(45) Date of Patent: Dec. 30, 2014

(54) ANTISEPTIC ALGINATE PREPARATION

(75) Inventors: Christian Rohrer, Villach (AT); Helmut Leuprecht, Vienna (AT); Corneliu Iulian Alupei, Melsbach (DE)

(73) Assignee: Lohmann & Rauscher GmbH & Co. KG, Neuwied (DE)

( * ) Notice: Subject to any disclaimer, the term of this patent is extended or adjusted under 35 U.S.C. 154(b) by 1277 days.

(21) Appl. No.: 12/161,061

(22) PCT Filed: Dec. 22, 2006

(86) PCT No.: PCT/EP2006/012525
§ 371 (c)(1),
(2), (4) Date: Dec. 4, 2008

(87) PCT Pub. No.: WO2007/087888
PCT Pub. Date: Aug. 9, 2007

(65) Prior Publication Data
US 2009/0306157 A1  Dec. 10, 2009

(30) Foreign Application Priority Data
Jan. 16, 2006  (DE) .......... 10 2006 001 954

(51) Int. Cl.
*A61K 31/428* (2006.01)
*A61K 31/155* (2006.01)
*A61L 15/46* (2006.01)
*A61L 15/20* (2006.01)
*A61L 15/28* (2006.01)

(52) U.S. Cl.
CPC .......... *A61L 15/46* (2013.01); *A61L 15/20* (2013.01); *A61L 15/28* (2013.01); *A61L 2300/204* (2013.01); *A61L 2300/206* (2013.01); *A61L 2300/404* (2013.01)
USPC .......... 514/635; 514/373

(58) Field of Classification Search
CPC ......... A61L 15/28; A61L 15/20; A61L 15/46; A61L 2300/204; A61L 2300/206; A61L 2300/404; C08L 5/04
USPC .......... 514/635, 373
See application file for complete search history.

(56) References Cited

U.S. PATENT DOCUMENTS

| 5,470,576 | A | 11/1995 | Patel |
| 5,690,955 | A | 11/1997 | Griffiths |
| 5,693,624 | A | 12/1997 | Hardy et al. |
| 2004/0028722 | A1 | 2/2004 | Serafica et al. |
| 2004/0082925 | A1* | 4/2004 | Patel ............... 604/289 |

FOREIGN PATENT DOCUMENTS

| EP | 0 650 373 B1 | 9/1996 | |
| EP | 0 680 525 B1 | 5/1997 | |
| EP | 0 532 275 B1 | 1/1999 | |
| EP | 0 613 692 B1 | 1/1999 | |
| EP | 0 586 260 B1 | 10/1999 | |
| EP | 0 797 430 B1 | 5/2003 | |
| EP | 0 783 605 B1 | 12/2003 | |
| EP | 1 435 247 B1 | 11/2006 | |
| WO | 94/17227 A1 | 8/1994 | |
| WO | 96/17595 A1 | 6/1996 | |
| WO | 02/36866 A1 | 5/2002 | |
| WO | 03/022317 A1 | 3/2003 | |
| WO | WO2005115357 | * 12/2005 | ............. A61K 31/00 |

OTHER PUBLICATIONS

McDonnell et al. (Clinical Microbiology Review, vol. 12 (1) 1999, pp. 147-149.*
Goswami et al. (Pharmainfo.net, Prospects in lyophilization, 2005, pp. 1-16, retrieved from internet on Jan. 4, 2011, URL: http://www.pharmainfo.net/reviews/prospects-lyophilization.*

* cited by examiner

*Primary Examiner* — Savitha Rao
(74) *Attorney, Agent, or Firm* — Panitch Schwarze Belisario & Nadel LLP

(57) ABSTRACT

An antiseptic preparation is provided for the production of wound dressings or bandages. The preparation includes at least one alginate and at least one antiseptically active substance selected from the group biguanide derivatives, octenidine and taurolidine. Processes for the production of the antiseptic preparations, and the use thereof, are also provided.

17 Claims, No Drawings

ANTISEPTIC ALGINATE PREPARATION

CROSS-REFERENCE TO RELATED APPLICATIONS

This application is a Section 371 of International Application No. PCT/EP2006/012525, filed Dec. 22, 2006, which was published in the German language on Aug. 9, 2007, under International Publication No. WO 2007/087888 A3 and the disclosure of which is incorporated herein by reference.

BACKGROUND OF THE INVENTION

The present invention relates to preparations that are suitable for the manufacture of wound dressings or bandages and comprise at least one alginate and at least one antiseptically active substance.

The invention furthermore relates to processes for the production of antiseptically active alginate preparations, and the use thereof.

The salts of alginic acid are called alginates. Alginic acid is a colorless, carboxyl groups-containing polysaccharide of 1,4-glycosidally linked D-mannuronic acid units with occasional insertions of L-guluronic acid, and falls into the group of the polyuronic acids. Alginic acid can account for up to 40 wt. % of the dry matter of brown algae. The alkali salts of alginic acid, the ammonium salt of alginic acid, and the magnesium salt of alginic acid are water-soluble. In particular, sodium alginate, also called algine, is of great importance as a thickening agent, emulsifier or emulsion stabilizer, and as a basis for gels, in the food, pharmaceutical and cosmetics industries. By contrast, calcium alginate and zinc alginate are water-insoluble, just as is alginic acid. By adding water-insoluble calcium alginate to sodium alginate gels it is possible to increase the viscosity of the latter.

The use of calcium alginate for the production of alginate fibers, and of wound dressings made of alginate fibers, is already known. Alginate fibers are produced by extracting alginic acid from algae by means of a soda solution. The resultant sodium alginate solution is purified and pressed into a precipitation bath containing a weakly acid $CaCl_2$ solution.

European patent application publication EP 0 586 260 A1 describes alginate gels in the form of a fibrous paste, which has an alginate content of 2 to 11 wt. %. and which is produced by treating water-insoluble or water-swellable alginate fibers with an aqueous solution of a solubilizing salt.

U.S. Pat. No. 5,470,576 discloses a process for the production of alginate-containing wound dressings, wherein a soft, absorbent fabric is impregnated with an alginate by immersing the fabric into an aqueous sodium alginate solution, to which calcium chloride is subsequently added in order to precipitate calcium alginate. These wound dressings are intended to have a haemostatic effect upon contact with the wound.

European Patent EP 0 783 605 B1 describes wound dressings which contain alginate fibers and are produced by co-spinning and solidification of an alginate and a water-soluble carboxymethyl cellulose. The alginate has a cross-linked form, and the alginate from which the fibers are co-spun has a G-content of at least 35 wt. %.

European patent application publication EP 1 435 247 A1 relates to a multilayer wound dressing comprising a fabric of alginate fibers and a layer which is not to be brought into contact with the wound and contains a superabsorbent.

Wound dressings or bandages of natural alginate fibers have good absorption capacity for wound exudate. Because of this, wound dressings of this type are also suitable for the wound management of highly exuding wounds, such as ulcers, decubital ulcers and fresh split-thickness skin removals, as well as for the wound management of infected wounds. Their high exudation absorptivity enables dressings to be changed at greater intervals.

It is particularly advantageous that wound dressings of alginate fibers form a gel upon contact with wound exudate or blood. This enables the wound dressing to conform to the contours of the wound and also to bind bacteria, contained in the exudate, in the gel. The wound is continuously maintained in a moist condition, epithelium can develop readily, and, due to an optimal microclimate, wound healing is accelerated.

Another advantage of wound dressings or bandages of natural alginate fibers is that they do not stick to the skin. Consequently, the young tissue is not damaged when the dressing or bandage is changed, and the healing process is not interrupted.

Wounds contaminated with or infected by pathogens must, however, be treated antiseptically as well, because:
  infection may develop as long as the wound is colonized,
  the wound healing process remains incomplete, or is completed with a delay only, as long as the wound remains infected,
  the infection of the wound may spread and lead to sepsis, and
  in the case of a colonization of the wound with multi-resistant germs, the spreading of the pathogens must be prevented.

In the case of burn wounds, too, there is a necessity of early prevention of wound infections, especially where contamination of larger wound areas is to be expected.

There is thus a need for wound dressings or bandages for wound management that enable antiseptic wound treatment.

However, the treatment of acute and chronic wounds with local therapeutics, especially with antiseptics, is presently regarded as being appropriate only for special indications, since many of the established antiseptics are considered unacceptable on assessment of their cost-benefit-risk ratio. Modern local antiseptics, which in contrast to the above, afford a broad spectrum of activity and good tolerability are, for example, octenidine and polyhexanide (=polyhexamethylene biguanide; PHMB). Short-term application of octenidine is supported especially in cases of microbially contaminated acute wounds, whereas polyhexanide is recommended instead for repeated applications on chronically slow-healing or sensitive wounds due to its comparatively slow onset of action. A disadvantage of the use of polyhexanide, however, is the fact that this antiseptic loses its efficacy in the presence even of small quantities of negatively charged ions.

International application publication WO 02/36866 A1 discloses polysaccharide fibers having water-absorbent properties, preferably of alginate or of a combination of alginate and another polysaccharide material, for example absorption-enhancing carboxymethyl cellulose, which fibers contain a silver compound as an antimicrobially active agent. WO 02/36866 A1 also describes wound dressings made from these polysaccharide fibers.

International application publication WO 03/022317 A1 describes an antibacterial wound dressing based on gel-forming fibers, such as carboxymethyl cellulose or alginate fibers, to which silver ions are bound uniformly, via part of the available reversible binding sites for cations.

The use of silver and silver compounds in wound treatment is considered largely outdated, because of the short-term stability of the commonly employed preparations, because of possible absorption of silver ions, and because of superficial destruction of the skin by protein coagulation.

BRIEF SUMMARY OF THE INVENTION

An object of the present invention was therefore to provide a wound dressing or a bandage for antiseptic treatment of wounds, which has good antimicrobial activity, with which the principle of moist wound treatment can be continued, which does not adversely affect wound healing, and which is well tolerated, so that the concerns existing with regard to the long-established preparations do not apply to these wound dressings.

This object is, surprisingly, achieved with a preparation that contains at least one alginate and at least one antiseptically active substance selected from the group comprising biguanide derivatives, octenidine and taurolidine.

The subject matter of the present invention is thus a preparation based on alginate fibers, which comprises at least one antiseptic selected from the group comprising biguanide derivatives, octenidine and taurolidine.

The alginate fibers preferably are calcium alginate fibers, but zinc alginate fibers are also suitable. The preparations containing alginate fibers may be provided in the form of loose fibers or in the form of a fiber composite, preferably a loose fiber composite, e.g. a card sliver, or in the form of a textile fabric, e.g. as a nonwoven, web, woven, or knitted fabric.

DETAILED DESCRIPTION OF THE INVENTION

In its simplest embodiment the preparation according to the invention exclusively comprises alginates as the non-antiseptically active material. However, the preparation according to the present invention may also be a combination of antiseptically impregnated alginate fibers with additional materials that are suitable for the production of wound dressings. Materials suitable for combination with alginate fibers include, for example, collagen-based materials, cellulose and cellulose derivatives, especially carboxymethyl cellulose, pectins, as well as synthetic fibers and so-called superabsorbents, which, preferably, are polyacrylates. These materials may also be equipped with an antiseptically active agent before they are further processed together with alginate fibers into the desired products.

In these embodiments, the portion of alginate fibers, relative to the weight of the non-antiseptically active components of the preparation, may be 5 to 95 wt. %. On a quantity basis, the alginate fibers preferably account for the larger part of the non-antiseptically active components of the preparation. In these embodiments, the proportion of alginate fibers is 50 to 95 wt. %., preferably 60 to 90 wt. %., and particularly preferably 70 to 80 wt. %. Consequently, the proportion of the additional non-antiseptically active materials is 5 to 50 wt. %., preferably 10 to 40 wt. %. and particularly preferably 20 to 30 wt. %.

However, embodiments wherein the portion of alginate fibers in the combination of alginate fibers and other materials is 50 wt. %. or less, relative to the weight of the non-antiseptically active components of the preparation, are also possible. In these embodiments the portion of alginate fibers is 5 to 50 wt. %., preferably 10 to 40 wt. %., and particularly preferably 20 to 30 wt. %., relative to the weight of the non-antiseptically active components of the preparation. In these embodiments the portion of the additional, non-antiseptically active material is 50 to 95 wt. %., preferably 60 to 90 wt. %., and particularly preferably 70 to 80 wt. %., likewise relative to the weight of the non-antiseptically active components of the preparation.

The preparation embodiments according to the present invention may also be provided in the form of alginate solutions or alginate gels. Preferably, the alginate gels are a mixture of sodium alginates and calcium alginate, so that the gels have the desired viscosity.

In a particularly preferred embodiment, the preparation according to the invention is present as a lyophilizate of an alginate solution.

The preparation according to the invention comprises at least one water-soluble, antiseptically active substance from the group comprising biguanide derivatives, octenidine and taurolidine. Suitable antiseptically active substances include, for example, the salts of chlorhexidine, the salts of octenidine, or the salts of polyhexamethylene biguanide. Examples of suitable salts are chlorhexidine dihydrochloride, chlorhexidine diacetate, chlorhexidine D-digluconate, octenidine dihydrochloride, octenidine disaccharin and the particularly preferable polyhexamethylene biguanide hydrochloride.

The antiseptically active substance is preferably contained in the preparation in an amount of 0.1 to 40 wt. %. and more preferably in an amount of 0.5 to 10 wt. %., relative to the dry weight of the alginate preparation.

The preparations according to the present invention may be produced by direct impregnation of the alginate fibers with the antiseptic, namely by impregnating the alginate fibers with the antiseptic prior to processing into the desired products. However, it is also possible to impregnate the finished product, for example the wound dressing, with the antiseptic.

For impregnation, the alginate fibers, or the product made of, or with the aid of, the alginate fibers and possibly containing further materials, may be treated by spraying with an antiseptic-containing solution or by immersing and/or rotating the alginate fibers, or the product, in an antiseptic-containing solution, so that the alginate fibers, or products, soaked with the antiseptic, have the desired content of antiseptic after drying.

It is also possible, however, to impregnate the alginate fibers with an antiseptic during their production, by providing the antiseptic already in the precipitation bath, or by dripping or spraying it on the wet-spun alginate fibers immediately prior to drying thereof.

Water is preferably used as the solvent for the antiseptic, but other, pharmacologically acceptable solvents are also suitable. Apart from buffer solutions, ethanol can be used, for example, as well as any mixtures of suitable solvents.

EXAMPLE 1

Pieces of 10 cm×10 cm (weight: 1 g) of a pad of calcium alginate fibers (SFM Limited) were placed in a dish and moistened with 20 ml of an aqueous PHMB solution (Cosmocil QC, 10 mg PHMB absolute; Arch Chemicals). To obtain a 1% load of the pad with antiseptic, a piece of the pad was moistened uniformly over the entire surface thereof with 10 times the mass of a 0.1% PHMB solution, using a pipette, and dried for 20 min at 65° C. in the dish. The moistened pieces were impregnated with PHMB by drying until completely dry, then packed and subsequently sterilized by exposure to gamma rays. The other PHMB loads prepared and employed within the framework of these tests are listed in Table 1.

The antimicrobial activity of the PHMB-impregnated wound dressings was examined by agar diffusion tests.

To this end, three clinical isolates (*Staphylococcus aureus* (ATCC 6538P), *Pseudomonas aeruginosa* (ATCC 9027) and *Candida albicans* (ATCC 10231)) are cultivated for 24 h at 30 to 35° C. in a non-selective liquid medium, and subsequently diluted with a 1% NaCl solution, containing 1% peptone, to $1 \times 10^8$ CFU/ml (colony forming units) and $3.8 \times 10^7$ CFU/ml (*C. albicans*), respectively. 100 µl of each dilution was spread on CSA and SDA plates, respectively (CSA=casein soy peptone agar; SDA=Sabouraud dextrose agar). The agar plates were dried for 3 to 5 minutes.

Test plates (diameter 34 mm) of the impregnated wound dressings were transferred with sterile forceps to the respective agar plates, which were subsequently covered with 400 µl of a 0.5% NaCl solution. The plates were incubated for 24 hr. at 30 to 35° C. and for 48 hr. at 20 to 25° C. (*Candida albicans*), respectively, before the zone of inhibition was determined.

The zone of inhibition was quantified by deducting the diameter of the test plate from the diameter of the clear inhibiting areola and dividing the resultant value by two. The result corresponds to the distance between the edge of the plate and the limit of the inhibiting areola and is indicated in mm. The results are listed in Table 1.

TABLE 1

Antiseptic activity of calcium alginate fiber fabric loaded with PHMB

| | Inhibition of propagation of | | |
|---|---|---|---|
| PHMB load | *S. aureus* | *P. aeruginosa* | *C. albicans* |
| 0.5% | 1 mm | 0 mm | 1-2 mm |
| 1.0% | 2-4 mm | 0-0.5 mm | 1-2 mm |
| 1.5% | 3-4 mm | 0-0.5 mm | 1-2 mm |
| 2.0% | 3-4 mm | 0-0.5 mm | 1-3 mm |

EXAMPLE 2

5 cm×5 cm pieces of a wound dressing of calcium alginate fibers (Suprasorb A; Lohmann und Rauscher) were moistened with ten times the mass of a PHMB solution, which contained 0.1, 0.5 or 1% of PHMB. The moistened wound dressings were deep-frozen at −50° C. and subsequently lyophilized. After lyophilization, the PHMB load of the impregnated wound dressings was 1, 5 and 10 wt. %., respectively.

The antimicrobial activity of the PHMB-impregnated wound dressings was examined by agar diffusion tests, as described in Example 1.

The PHMB-impregnated wound dressings of calcium alginate fibers showed a marked antiseptic activity against gram-negative *S. aureus*, even at a low PHMB load. The zone of inhibition surrounding the pieces increased with increasing PHMB load of the wound dressing.

In the case of *P. aeruginosa* (gram-positive), antiseptic activity could only be detected at higher PHMB loads. The zone of inhibition was small for all of the concentrations. But microbic contamination of the test plates was efficiently prevented at all PHMB loads.

A distinct zone of inhibition around the test plates was also observed in the tests with *C. albicans*.

These results show that by loading calcium alginates with polyhexanide it is possible to produce wound dressings having antiseptic activity. This is contrary to the general opinion held by the experts, according to which, if the cationic polyhexanide is employed, even small traces of negative charge, for example in the form of alginate, acrylate, lactate or iodide ions, will suffice to quickly inactivate the antiseptic action thereof.

By loading alginate fibers or products based on alginate fibers, it is possible to produce wound dressings or bandages that enable antiseptic wound treatment, while there is no necessity of having to do without the valued advantages afforded by the use of alginates.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An antiseptic alginate preparation for production of a wound dressing, the preparation comprising calcium alginate fibers that are impregnated with at least one antiseptically active substance selected from the group consisting of polyhexamethylene biguanide and salts of polyhexamethylene biguanide, wherein the at least one antiseptically active substance is present in the antiseptic alginate preparation in an amount of 0.5% to 10% by weight relative to a dry weight of the antiseptic alginate preparation, and wherein the antiseptic activity of the antiseptically active substance is not inactivated by the presence of the calcium alginate fibers.

2. The preparation according to claim 1, wherein the at least one antiseptically active substance is water-soluble.

3. The preparation according to claim 1, wherein the preparation comprises at least one additional material selected from the group consisting of collagen-based materials, pectin, cellulose and cellulose derivatives, synthetic fibers, and superabsorbers.

4. The preparation according to claim 3, wherein the additional material is present in an amount of 5 to 50 wt. %, relative to a weight of non-antiseptically active substances of the preparation.

5. The preparation according to claim 3, wherein the additional material is present in an amount of 50 to 95 wt. %, relative to a weight of non-antiseptically active substances of the preparation.

6. The preparation according to claim 1, wherein the preparation has a form selected from fibers, fiber composites, textile fabrics, solutions, gels, and lyophilizates.

7. A process for preparing an antiseptic alginate preparation, the process comprising:
impregnating calcium alginate fibers with at least one antiseptically active substance selected from the group consisting of polyhexamethylene biguanide and salts of polyhexamethylene biguanide, wherein the impregnating step comprises one of the following:
spraying, soaking or dripping the calcium alginate fibers, or products made from the calcium alginate fibers, with a solution of the at least one antiseptically active substance; and
obtaining the calcium alginate fibers from a precipitation bath containing the at least one antiseptically active substance;
and subsequently drying the calcium alginate fibers,
wherein the at least one antiseptically active substance is present in the obtained antiseptic alginate preparation in an amount of 0.5% to 10% by weight relative to a dry weight of the antiseptic alginate preparation, and wherein the antiseptic activity of the antiseptically active substance is not inactivated by the presence of the calcium alginate fibers.

8. The process according to claim 7, wherein drying is effected by lyophilization.

9. The preparation according to claim 1, wherein the preparation is present in one of a wound dressing and a bandage material.

10. A wound dressing or bandage comprising an antiseptic alginate preparation, the preparation comprising calcium alginate fibers that are impregnated with at least one antiseptically active substance selected from the group consisting of polyhexamethylene biguanide and salts of polyhexamethylene biguanide, wherein the at least one antiseptically active substance is present in the antiseptic alginate preparation in an amount of 0.5% to 10% by weight relative to a dry weight of the antiseptic alginate preparation, and wherein the antiseptic activity of the antiseptically active substance is not inactivated by the presence of the calcium alginate fibers.

11. The preparation according to claim 1, wherein the calcium alginate fibers are impregnated with polyhexamethylene biguanide hydrochloride.

12. The preparation according to claim 1, wherein the preparation exhibits antimicrobial activity against *Staphylococcus aureus, Pseudomonas aeruginosa*, and *Candida albicans*.

13. The process according to claim 7, wherein the at least one antiseptically active substance comprises polyhexamethylene biguanide hydrochloride.

14. The preparation according to claim 1, wherein the calcium alginate fibers are present in an amount of 50% to 95% by weight relative to a weight of non-antiseptically active substances.

15. The wound dressing or bandage according to claim 10, wherein the calcium alginate fibers are present in an amount of 50% to 95% by weight relative to a weight of non-antiseptically active substances.

16. The preparation according to claim 1 consisting of calcium alginate fibers impregnated with polyhexamethylene biguanide, wherein polyhexamethylene biguanide is present in an amount of 0.5% to 10% by weight relative to a dry weight of the calcium alginate fibers.

17. The wound dressing or bandage according to claim 10, wherein the antiseptic alginate preparation consists of calcium alginate fibers impregnated with polyhexamethylene biguanide, wherein polyhexamethylene biguanide is present in an amount of 0.5% to 10% by weight relative to a dry weight of the calcium alginate fibers.

* * * * *